(12) United States Patent
Bhullar et al.

(10) Patent No.: US 7,867,369 B2
(45) Date of Patent: Jan. 11, 2011

(54) BIOSENSOR WITH MULTIPLE ELECTRICAL FUNCTIONALITIES

(75) Inventors: Raghbir S. Bhullar, Indianapolis, IN (US); Harvey B. Buck, Jr., Indianapolis, IN (US); Brian S. Hill, Avon, IN (US); Paul Douglas Walling, Indianapolis, IN (US); Terry A. Beaty, Indianapolis, IN (US); David W. Burke, Carmel, IN (US); Eric R. Diebold, Noblesville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1468 days.

(21) Appl. No.: 10/871,843

(22) Filed: Jun. 18, 2004

(65) Prior Publication Data

US 2005/0023137 A1    Feb. 3, 2005

Related U.S. Application Data

(60) Provisional application No. 60/480,243, filed on Jun. 20, 2003.

(51) Int. Cl.
   *G01N 27/327*    (2006.01)
(52) U.S. Cl. .................. 204/403.02; 204/403.01; 204/406
(58) Field of Classification Search .......... 204/403, 204/406, 418, 403.01, 403.02, 403.03, 403.13; 435/817, 288, 291

See application file for complete search history.

(56) References Cited

U.S. PATENT DOCUMENTS

| | | | | |
|---|---|---|---|---|
| 4,713,165 A | * | 12/1987 | Conover et al. | 204/403.05 |
| 5,120,420 A | * | 6/1992 | Nankai et al. | 204/403.11 |
| 5,312,762 A | * | 5/1994 | Guiseppi-Elie | 205/778 |
| 5,384,028 A | * | 1/1995 | Ito | 257/253 |
| 5,672,256 A | | 9/1997 | Yee | |

(Continued)

FOREIGN PATENT DOCUMENTS

DE        102 22 428 A1    12/2002

(Continued)

OTHER PUBLICATIONS

Canadian Patent Application No. 2,529,579 Office Action mailed Nov. 26, 2009.

(Continued)

*Primary Examiner*—Kaj K Olsen
(74) *Attorney, Agent, or Firm*—Woodard, Emhardt, Moriarty, McNett & Henry LLP

(57) ABSTRACT

A biosensor having multiple electrical functionalities located both within and outside of the measurement zone in which a fluid sample is interrogated. Incredibly small and complex electrical patterns with high quality edges provide electrical functionalities in the biosensor and also provide the electrical wiring for the various other electrical devices provided in the inventive biosensor. In addition to a measurement zone with multiple and various electrical functionalities, biosensors of the present invention may be provided with a user interface zone, a digital device zone and/or a power generation zone. The inventive biosensors offer improved ease of use and performance, and decrease the computational burden and associated cost of the instruments that read the biosensors by adding accurate yet cost-effective functionalities to the biosensors themselves.

79 Claims, 7 Drawing Sheets

U.S. PATENT DOCUMENTS

| | | | |
|---|---|---|---|
| 5,677,546 A * | 10/1997 | Yu | 257/40 |
| 5,766,789 A * | 6/1998 | James et al. | 429/44 |
| 5,869,972 A | 2/1999 | Birch et al. | |
| 5,897,522 A * | 4/1999 | Nitzan | 604/20 |
| 5,942,102 A * | 8/1999 | Hodges et al. | 205/775 |
| 6,274,326 B1 | 8/2001 | Stoughton | |
| 6,300,141 B1 * | 10/2001 | Segal et al. | 435/287.1 |
| 6,319,719 B1 | 11/2001 | Bhullar et al. | |
| 6,331,438 B1 * | 12/2001 | Aylott et al. | 436/172 |
| 6,561,978 B1 * | 5/2003 | Conn et al. | 600/309 |
| 6,743,635 B2 * | 6/2004 | Neel et al. | 436/95 |
| 6,814,844 B2 | 11/2004 | Bhullar et al. | |
| 7,022,218 B2 | 4/2006 | Taniike et al. | |
| 7,041,206 B2 | 5/2006 | Gephart et al. | |
| 2001/0028032 A1 * | 10/2001 | Church et al. | 250/227.14 |
| 2002/0072784 A1 * | 6/2002 | Sheppard et al. | 607/60 |
| 2002/0100685 A1 * | 8/2002 | Huang et al. | 204/403.07 |
| 2002/0170823 A1 * | 11/2002 | Housefield et al. | 204/403.01 |
| 2002/0177763 A1 | 11/2002 | Burns et al. | |
| 2002/0192115 A1 | 12/2002 | Bhullar et al. | |
| 2003/0004403 A1 * | 1/2003 | Drinan et al. | 600/301 |
| 2003/0062263 A1 * | 4/2003 | Stanford et al. | 204/403.01 |
| 2003/0146436 A1 * | 8/2003 | Parker et al. | 257/72 |
| 2003/0155237 A1 * | 8/2003 | Surridge et al. | 204/403.14 |
| 2003/0159945 A1 * | 8/2003 | Miyazaki et al. | 205/777.5 |
| 2003/0175946 A1 | 9/2003 | Tokunaga et al. | |
| 2003/0185705 A1 * | 10/2003 | Otake | 422/58 |
| 2004/0118681 A1 * | 6/2004 | Hellinga et al. | 204/403.01 |
| 2004/0157337 A1 * | 8/2004 | Burke et al. | 436/70 |
| 2004/0244151 A1 | 12/2004 | Sakata et al. | |
| 2004/0251131 A1 | 12/2004 | Ueno | |
| 2005/0258034 A1 | 11/2005 | Iketaki et al. | |
| 2008/0314882 A1 | 12/2008 | Bhullar et al. | |

FOREIGN PATENT DOCUMENTS

| | | |
|---|---|---|
| EP | 0 471 986 B1 | 2/1992 |
| EP | 1 253 204 A2 | 10/2002 |
| EP | 1 431 758 A1 | 6/2004 |
| JP | 2001-66279 A | 6/1990 |
| JP | 2000-019147 | 1/2000 |
| JP | 2002-535615 A | 10/2002 |
| JP | 2003-014687 A | 1/2003 |
| JP | 2003-511851 | 3/2003 |
| JP | 2003-149192 A | 5/2003 |
| JP | 2006-509187 A | 3/2006 |
| WO | WO 00/33063 | 6/2000 |
| WO | WO 00/42422 A1 | 7/2000 |
| WO | WO 01/25775 A1 | 4/2001 |
| WO | WO 02/054055 A1 | 7/2002 |
| WO | WO 02/057768 A1 | 7/2002 |
| WO | WO 02/086483 A1 | 10/2002 |
| WO | 03/029804 A1 | 4/2003 |
| WO | WO 03/056345 A1 | 7/2003 |
| WO | WO 2004/034053 A2 | 4/2004 |

OTHER PUBLICATIONS

Japanese Patent Application No. 517450/2006 Office Action mailed Dec. 15, 2009.

U.S. Appl. No. 10/872,027 to Bhullar et al., Office Action mailed Jun. 15, 2010.

Niwa, Osamu et al.; Electrochemical Behavior of Reversible Redox Species at Interdigitated Array Electrodes with Different Geometries: Consideration of Redox Cycling and Collection Efficiency; Anal. Chem.; 1990; 447-452; 62; Ibaraki, Japan.

Tanaka, Mitsuya et al.; Voltammetry at Geometrically Uneven Electrodes: Part 1, Chronoamperometry at Model Electrodes with Rectangular Hollow or Protrusive Surfaces; J. Electroanal. Chem.; 1988; 1-14; 246; The Netherlands.

Aoki, Koichi and Tanaka, Mitsuya; Time-Dependence of Diffusion-Controlled Currents of a Soluble Redox Couple at Interdigitated Microarray Electrodes; J. Electroanal. Chem.; 1989; 11-20; 266; The Netherlands.

Aoki, Koichi; Theory of the Steady-State Current of a Redox Couple at Interdigitated Array Electrodes of Which Pairs are Insulated Electrically by Steps; J. Electroanal. Chem.; 1989; 35-41; 270; The Netherlands.

Aoki, Koichi; Approximate Models of Interdigitated Array Electrodes for Evaluating Steady-State Currents; J. Electroanal. Chem.; 1990; 35-42; 284; The Netherlands.

Aoki, Koichi et al.; Theory of Charge Transport Within Polymer Films With Uneven Thickness Coated on Electrodes; J. Electroanal. Chem.; 1984; 139-150; 176; The Netherlands.

Aoki, Koichi et al.; Reversible Square-Wave Voltammograms: Independence of Electrode Geometry; J. Electroanal. Chem.; 1986; 25-39; 207; The Netherlands.

Matsuda, Hiroaki et al.; Theory of Electrode Reactions of Redox Couples Confined to Electrode Surfaces at Monolayer Levels; Part I. Expression of the Current-Potential Relationship for Simple Redox Reactions; J. Electroanal. Chem.; 1987; 1-13; 217; The Netherlands.

Matsuda, Hiroaki et al.; Theory of Electrode Reactions of Redox Couples Confined to Electrode Surfaces at Monolayer Levels; Part II. Cyclic Voltammetry and AC Impedance Measurements: J. Electroanal. Chem.; 1987; 15-32; 217; The Netherlands.

Aoki, Koichi et al.; Theory of Chromoamperometric Curves at Microband Electrodes; J. Electroanal. Chem.; 1987; 19-32; 225; The Netherlands.

Aoki, Koichi et al.; Derivation of an Approximate Equation for Chronoamperometric Curves at Microband Electrodes and its Experimental Verification; J. Electroanal. Chem.; 1987; 61-67; 230; The Netherlands.

Aoki, Koichi et al.; Quantitative Analysis of Reversible Diffusion-Controlled Currents of Redox Soluble Species at Interdigitated Array Electrodes Under Steady-state Conditions; J. Electroanal. Chem.; 1988; 269-282; 256; The Netherlands.

Aoki, Koichi et al.; Derivation of an Approximate Equation for Chronoamperometric Curves at Microbank Electrodes and Its Experimental Verification; J. Electroanal. Chem.; 1987; 61-67; 230; The Netherlands.

Aoki, Koichi et al.; Theory of Chronoamperometric Curves at Microband Electrodes; J. Electroanal. Chem.; 1987; 19-32; 225; The Netherlands.

Chidsey, Christopher E. et al.; Micrometer-Spaced Platinum Interdigitated Array Electrode: Fabrication, Theory, and Initial Use; Anal. Chem.; 1986; 601-607; 58; Murray Hill, NJ, US.

Feldman, B.J. et al.; Electron Transfer Kinetics at Redox Polymer/Solution Interfaces Using Microelectrodes and Twin Electrode Thin Layer Cells; J. Electroanal. Chem.; 1985; 63-81; 194; The Netherlands.

Feldman, B.J. and Murray, Royce W.; Electron Diffusion in Wet and Dry Prussian Blue Films on Interdigitated Array Electrodes; Amer. Chem. Soc.; 1987; 1702-1708; 26; Chapel Hill, NC, US.

Feldman, B.J. and Murray, Royce W.; Measurement of Electron Diffusion Coefficients Through Prussian Blue Electroactive Films Electrodeposited on Interdigitated Array Platinum Electrodes; Amer. Chem. Soc.; 1986; 2844-2847; 58; Chapel Hill, NC, US.

Anderson, Larry B. and Reilley, Charles N.; Thin-Layer Electrochemistry: Steady-State Methods of Studying Rate Processes; J. Electroanal. Chem.; 1965; 295-305; 10; Chapel Hill, NC, US.

Kirowa-Eisener, H. Reller E. and Gileadi, E.; Ensembles of Microelectrodes: A Digital Simulation; J. Electroanal. Chem.; 1982; 65-77; 138; The Netherlands.

Anderson, James L. et al.; Hydrodynamic Voltammetry at an Interdigitated Electrode Array in a Flow Channel: *Part I. Numerical Simulation*; J. Electroanal. Chem.; 1985; 213-226; 196; The Netherlands.

Aoki, Koichi and Osteryoung, Janet; Diffusion Controlled Current at a Stationary Finite Disk Electrode: Experiment; J. Electoanal. Chem.; 1981; 315-320; 125; The Netherlands.

Aoki, Hoichi et al.; Quantitative Analysis of Reversible Diffusion-Controlled Currents of Redox Soluble Species at Interdigitated Array Electrodes Under Steady-State Conditions; J. Electroanal. Chem.; 1988; 269-282; 256; The Netherlands.

Foster, Robert et al.; Electrochemical Diagnostic Strip Device for Total Cholesterol and Its Subfractions: Electroanalysis; 2000; 716-721; vol. 12; No. 9; Gwynedd; UK.

Niwa, Osamu et al.; Fabrication and Characteristics of Vertically Separated Interdigitated Array Electrodes; J. Electroanal. Chem.; 1989; 291-297; 267; The Netherlands.

Horluchl, Tsutomu et al.; Detection of Reversible Redox Species by Substitutional Stripping Voltammetry; Anal. Chem.; 1994; 1224-1230; 66; Ibaraki, Japan.

Power Paper Ltd.; MK3B Power Paper Primary Cell.

Dick, David J. et al; Imaging the Structure of the P-N. Junction in Polymer Light-Emitting Electrochemical Cells; Advanced materials 1996.

Anderson, J.D. et al; Electrochemistry and Electrogenerated Chemiluminescence Processes of the Components of Aluminum Quinolate/Triarylamine, and Related Organic Light-Emitting Diodes; American Chemical Society, 1998.

Gross, E.M. et al; Electrogenerated Chemiluminescence from Derivatives of Aluminum Quinolate and Quinacridones: Cross-Reactions with Triarylamines Lead to Singlet Emission through Triplet-Triplet Annihilation Pathways; American Chemical Society, 2000.

Olivier, Stephan et al.; Blue-Green Light Emitting Diodes and Electrochemical Cells Based on a Copolymer Derived From Fluorene; Synthetic Metals, 2000.

Japanese Patent Application No. 2000-019147 Machine Translation.

Japanese Patent Application No. 2001-66279 English Language Abstract.

Japanese Patent Application No. 517450/2006 Office Action mailed May 26, 2009.

* cited by examiner

BIOSENSOR WITH MULTIPLE ELECTRICAL FUNCTIONALITIES

REFERENCE TO RELATED APPLICATIONS

This application claims priority to U.S. Provisional Patent Application No. 60/480,243 entitled "DEVICES AND METHODS RELATING TO ELECTROCHEMICAL BIOSENSORS," filed Jun. 20, 2003. This application is also related to applications entitled TEST STRIP WITH SLOT VENT OPENING ("Slot Vent Opening") Ser. No. 10/871,468, METHOD OF MAKING A BIOSENSOR Ser. No. 10/871,937, METHOD AND REAGENT FOR PRODUCING NARROW, HOMOGENEOUS REAGENT STRIPES ("Reagent Stripes") Ser. No. 10/871,966, SYSTEM AND METHOD FOR QUALITY ASSURANCE OF A BIOSENSOR TEST STRIP ("Quality Assurance") 60/581,002, SYSTEM AND METHOD FOR CODING INFORMATION ON A BIOSENSOR TEST STRIP ("Coding Information") Ser. No. 10/871,977, DISPENSER FOR FLATTENED ARTICLES ("Dispenser") Ser. No. 10/871,943, all of which have been filed on even date herewith and which are all incorporated herein by reference in their entireties. This application also is related to an application entitled SYSTEM AND METHOD FOR ANALYTE MEASUREMENT USING DOSE SUFFICIENCY ELECTRODES, filed Oct. 17, 2003 and given Ser. No. 10/687,958 ("Dose Sufficiency"), which is incorporated herein by reference in its entirety.

FIELD OF THE INVENTION

The present invention relates generally to devices, systems, and methods for measuring analytes from biological samples, such as from a sample of bodily fluid. More particularly, the present invention relates to electrically operable biosensors.

BACKGROUND

Measuring the concentration of substances, particularly in the presence of other, confounding substances ("interferents"), is important in many fields, and especially in medical diagnosis and disease management. For example, the measurement of glucose in bodily fluids, such as blood, is crucial to the effective treatment of diabetes.

Multiple methods are known for measuring the concentration of analytes such as glucose in a blood sample. Such methods typically fall into one of two categories: optical methods and electrochemical methods. Optical methods generally involve absorbance, reflectance or laser spectroscopy to observe the spectrum shift in the fluid caused by the concentration of the analytes, typically in conjunction with a reagent that produces a known color when combined with the analyte. Electrochemical methods generally rely upon the correlation between a charge-transfer or charge-movement property of the blood sample (e.g., current, interfacial potential, impedance, conductance, and the like) and the concentration of the analyte, typically in conjunction with a reagent that produces or modifies charge-carriers when combined with the analyte. See, for example, U.S. Pat. Nos. 4,919,770 to Preidel, et al., and 6,054,039 to Shieh, which are incorporated by reference herein in their entireties.

An important limitation of electrochemical methods of measuring the concentration of a chemical in blood is the effect of confounding variables on the impedance of a blood sample. For example, the geometry of the blood sample must correspond closely to that upon which the impedance-to-concentration mapping function is based.

The geometry of the blood sample is typically controlled by a sample-receiving chamber of the testing apparatus in which the fluid sample is received and held during its analysis. In the case of blood glucose meters, for example, the blood sample is typically placed onto a disposable test strip or biosensor that plugs into the meter. The test strip may have a sample chamber to define the geometry of the sample. Alternatively, the effects of sample geometry may be limited by assuring an effectively infinite sample size. For example, the electrodes used for measuring the analyte may be spaced closely enough so that a drop of blood on the test strip extends substantially beyond the electrodes in all directions. Regardless of the strategy used to control sample geometry, typically one or more dose sufficiency electrodes are used to assure that a sufficient amount of sample has been introduced into the sample receiving chamber to assure an accurate test result.

Other examples of limitations to the accuracy of blood glucose measurements include variations in blood chemistry (other than the analyte of interest being measured). For example, variations in hematocrit (concentration of red blood cells) or in the concentration of other chemicals, constituents or formed elements in the blood, may affect the measurement. Variation in the temperature of blood samples is yet another example of a confounding variable in measuring blood chemistry. In addition, certain other chemicals can influence the transfer of charge carriers through a blood sample, including, for example, uric acid, bilirubin, and oxygen, thereby causing error in the measurement of glucose.

Efforts to improve test strips have been mainly directed to making them smaller, faster, and require less sample volume. For example, it is desirable for electrochemical biosensors to be able to analyze as small a sample as possible, and it is therefore necessary to minimize the size of their parts, including the electrodes. Traditionally, screen-printing, laser scribing, and photolithography techniques have been used to form miniaturized electrodes. These methods are undesirably time-consuming, however, and screen-printing or laser scribing technologies pose limitations on the edge quality of the electrical patterns formed, such that gap widths between electrical elements normally must be 75 microns or more. Further, some of these techniques make it unworkable on a commercial scale to remove more than a small fraction, e.g., more than 5-10% of the conductive material from a substrate to form an electrical pattern.

The electrode structures in available electrochemical test strips made by these techniques typically have one or perhaps two pairs of electrodes, and the measurements obtained by these electrode structures are quite sensitive to the interferents discussed above. Thus, the signal produced by the analyte desired to be analyzed must be deconvoluted from the noise produced by the interfering substances. Many approaches have been employed to attenuate/mitigate interference or to otherwise compensate or correct a measured value. Often, multiple design solutions are employed to adequately compensate for the sensitivities associated with the chosen measurement method.

One approach involves removing interfering materials such as blood cells from the fluid sample before it reaches the electrodes by using perm-selective and/or size-selective membranes, filters or coatings. Multiple layers of membranes are often laminated together to achieve the ultimate goal of delivering a fluid to the electrodes which contains only low levels of interferents. Unfortunately, however, this approach suffers from incremental costs of goods, viz., coatings and membranes that must often be pre-treated prior to assembly. It also incurs additional manufacturing process steps that further increase manufacturing cost and complexity while decreasing the speed of manufacture. This approach addresses the attenuation problem by increasing the complexity and cost of the test strip, thereby reducing the burden of the meter which reads the strips.

Another general approach involves the use of sophisticated excitation and signal processing methods coupled with co-optimized algorithms. While simpler, less complex test strip architectures and manufacturing processes may be realized, instrumentation costs, memory and processor requirements, associated complex coding, and calibrated manufacturing techniques are all increased by this approach. Systems employing this approach address the attenuation problem by placing a higher computational burden on the meter that reads the strips.

Yet another more recent approach involves neither the strip nor instrumentation, per se, but rather exploits the measurement methodology. An example of this approach is the use of a coulometric method to attenuate the influence of hematocrit and temperature. This coulometric approach, however, requires a tight manufacturing tolerance on the volume of the sample receiving chamber in the test strips produced, since the entire sample is used during the analysis. Additionally, commercially available test strips using this technology require two separate substrates printed with electrodes, which further increases manufacturing costs. The requirement that much of the sample volume be interrogated may also limit test speed. Further, this approach requires relatively large electrodes to provide significant electrolysis of the sample in a relatively short time in order to estimate the "endpoint" of the coulometric detection.

It is also well known to those skilled in the art that all of the above approaches are further supported by the initial design of reagent systems. In the detection of glucose, for example, this may involve the use of selective redox mediators and enzymes to overcome the detrimental influence of redox-active species or the presence of other sugars.

It would be desirable to provide a simpler, less costly method for attenuating the influence of interferents, in a manner that does not suffer the demerits associated with the general approaches currently in wide use. It would also be desirable to provide a more functional, robust and user-friendly system for analyzing fluid samples, but without increasing the costs.

SUMMARY OF THE INVENTION

The present invention provides a biosensor having multiple electrical functionalities located both within and outside of the measurement zone in which the fluid sample is interrogated. Incredibly small and complex electrical patterns with high quality edges provide electrical functionalities in the biosensor and also provide the electrical wiring for the various other electrical devices provided in the inventive biosensor. In addition to a measurement zone with various electrode functionalities, biosensors of the present invention may be provided with a user interface zone, a digital device zone and/or a power generation zone.

The inventors of the present invention have taken an entirely different approach than the schemes discussed above for mitigating interference or otherwise correcting a value measured by a test strip. Their novel approach focuses upon (1) enhancing the quality and complexity of the electrical patterns formed on a biosensor, (2) significantly reducing the size of these electrical patterns, and at the same time (3) increasing production speeds while (4) reducing manufacturing costs. This approach decreases the computational burden and associated cost of the instruments that read the strips while at the same time adding accurate yet cost-effective functionalities to the biosensors themselves.

In one form thereof, the present invention provides a biosensor for analyzing a fluid sample. The biosensor includes a biosensor body that defines a measurement zone having a sample receiving chamber in which is disposed a measurement electrode for detecting the presence or concentration of an analyte in the fluid sample. The measurement zone also includes a reagent that reacts with the fluid sample. The biosensor body further defines a user interface zone in which is disposed an electrically driven signal generator which emits a visible, audible or tactile signal upon occurrence of a triggering event.

In one preferred form, the signal generator comprises a light positioned on the test strip body which illuminates (or turns off) upon the occurrence of the triggering event. In another preferred form the signal generator comprises a light disposed proximate the sample receiving chamber and which illuminates the sample receiving chamber upon the occurrence of the triggering event. In another preferred form, the signal generator is a numerical display.

Any number of occurrences can constitute a "triggering event," including but not limited to insertion of the strip into a meter, a sufficient size dose being received in the sample receiving chamber, malfunction of test, non-functional test strip, etc. Furthermore, there may be a delay between the occurrence of the triggering event and the signal generator emitting the signal.

In another preferred form, the signal generator comprises an electrode set on which the OLED is coated. More preferably, the electrode set comprises a micro-electrode array with at least two electrode fingers having a gap of less than about 5 microns between them.

In another preferred form, the biosensor also includes a power generation zone in which is disposed a power generator. More preferably, the biosensor additionally includes a digital information zone in which is disposed at least one digital device.

BRIEF DESCRIPTION OF THE DRAWINGS

The above-mentioned and other advantages of the present invention, and the manner of obtaining them, will become more apparent and the invention itself will be better understood by reference to the following description of the embodiments of the invention taken in conjunction with the accompanying drawings, wherein.

Corresponding reference characters indicate corresponding parts throughout the several views.

DESCRIPTION OF THE PREFERRED EMBODIMENTS

For the purposes of promoting an understanding of the principles of the invention, reference will now be made to the specific embodiments illustrated herein and specific language will be used to describe the same. It will nevertheless be understood that no limitation of the scope of the invention is thereby intended. Any alterations and further modifications in the described processes or devices, and any further applications of the principles of the invention as described herein, are contemplated as would normally occur to one skilled in the art to which the invention relates.

Introduction

Generally, the test strips embodied by the present invention provide for testing of an analyte in a bodily or other fluid using multiple electrode functionalities that are provided on board the test strips. In the sample receiving chamber, multiple electrode sets can be formed which perform the same or different functions. The novel electrical features of the embodiments disclosed herein extend beyond the concept of "measurement functionalities," however. Indeed, it is helpful to view test strips embodying the present invention as having individual "zones," each zone including electrical devices having a specific functionality. For example, in addition to a measurement zone in which fluid sample is received and analyzed, test strips disclosed herein may provide user interface, digital, and power generation zones that have been hitherto unavailable in test strip architecture.

General Description

Zones.

Figure 1:
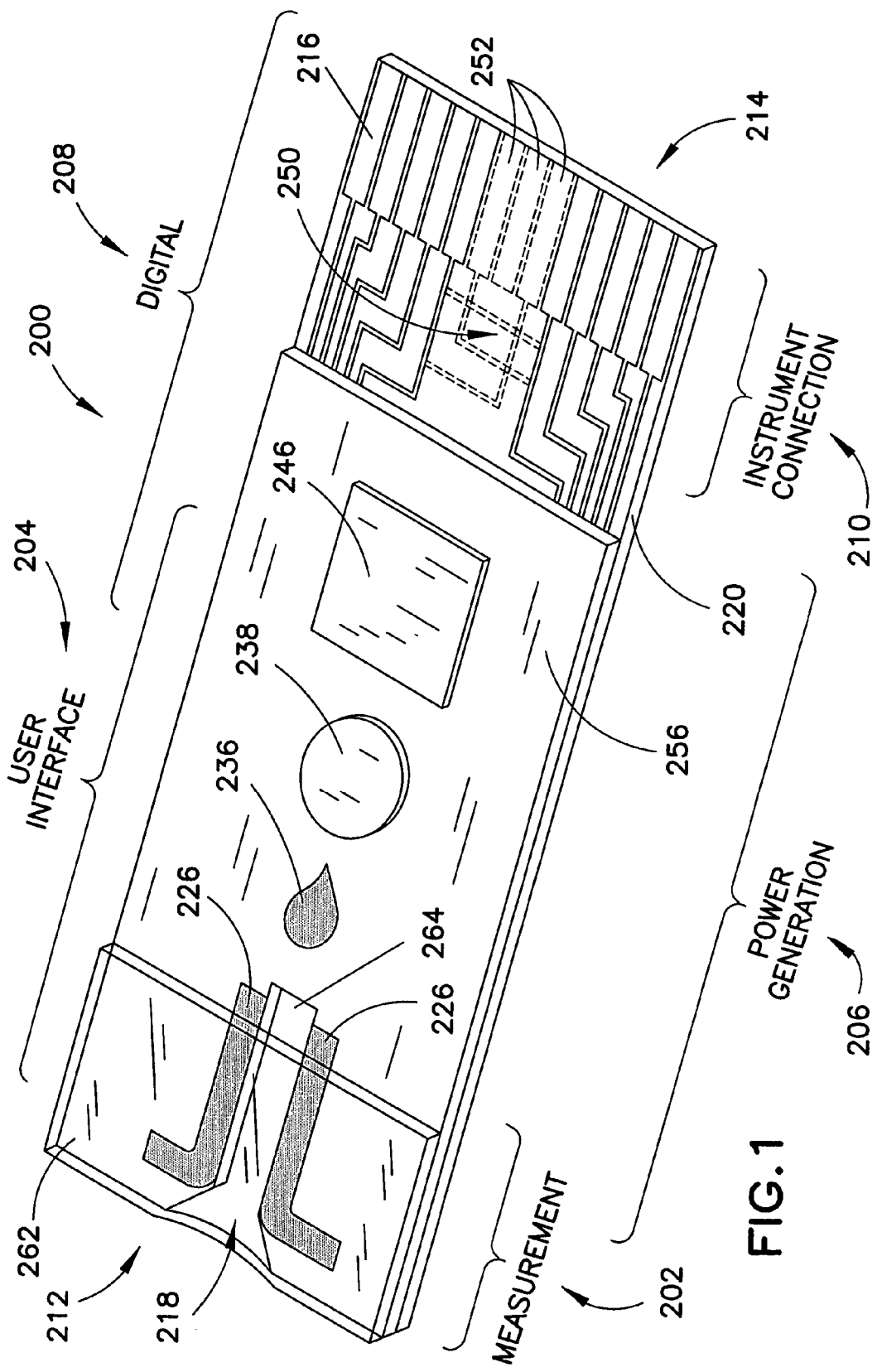
FIG. 1 is a perspective view of a biosensor or test strip in accordance with one embodiment of the present invention.

Turning now to FIG. 1, strip 200 defines a test strip body that generally has several zones, including a measurement zone 202, a user interface zone 204, a power generation zone 206, a digital device zone 208 and an instrument connection zone 210. As indicated in FIG. 1 and as will become clear with the discussion below, the zones are not limited to specific locations on a given test strip 200. Instead, the locations of the various zones will normally overlap to varying degrees as shown or may be discontinuous, occupying two or more different regions of the test strip body. Each zone generally has included therein electrical devices that perform a specific type or class of function.

For example, the electrical devices included in the measurement zone typically have functionalities related to the measurement (or correction of measurement) of the fluid sample being interrogated. Examples of these electrical devices include macro and micro-electrode sets, dose detection electrodes, sample sufficiency electrodes, temperature correction or temperature measurement electrodes, thermistors and the like. While the measurement zone is illustrated at a dosing end 212 of the strip, it should be understood that the measurement zone may alternatively occupy other locations on the strip, e.g., a side of the strip, as is known in the art.

The electrical devices in the user interface zone typically are electrically driven signal generators which emit a visible, audible or tactile signal upon occurrence of a "triggering event." As described in more detail below, the signal generator may be a light that illuminates or turns off after a sufficiently sized sample has been received in the measurement zone, the latter event being the "triggering event." The user interface zone is in some embodiments electrically wired to the measurement zone and/or other zones of the test strip.

The power generation zone includes one or more power generators that provide power to one or more other electrical devices disposed on or in the test strip. Typically, the power generator comprises a battery, but it could also comprise a capacitor or even a solar cell, depending upon the power requirements of the electrical device the power generator is going to drive and the specific functionality of that device.

Digital devices such as RFID tags, integrated circuits and the like are disposed within the digital zone and may be wired to the electrical pattern. In other embodiments, the electrical pattern that is disposed in the digital zone is itself encoded with digital information and thus comprises yet another type of digital device.

Finally, the instrument connection zone includes electrical devices, typically contact pads, that electrically link to an instrument (not shown) which includes driving circuitry and metering circuitry. The driving circuitry provides a known current and/or potential through contacts 216 and monitors the current and/or voltage response over a period of time. The metering circuitry correlates the monitored current, impedance and voltage response to estimated analyte concentration or other aspect of the analyte. While the instrument connection zone is preferably disposed on a meter insertion end 214 of the strip, this need not necessarily be the case. The instrument zone could be located on a side of the strip or could be located on the end as shown, but could also include contact pads that are disposed at various locations on the top, bottom or sides of the test strip.

Strip Architecture and Components.

Figure 2:
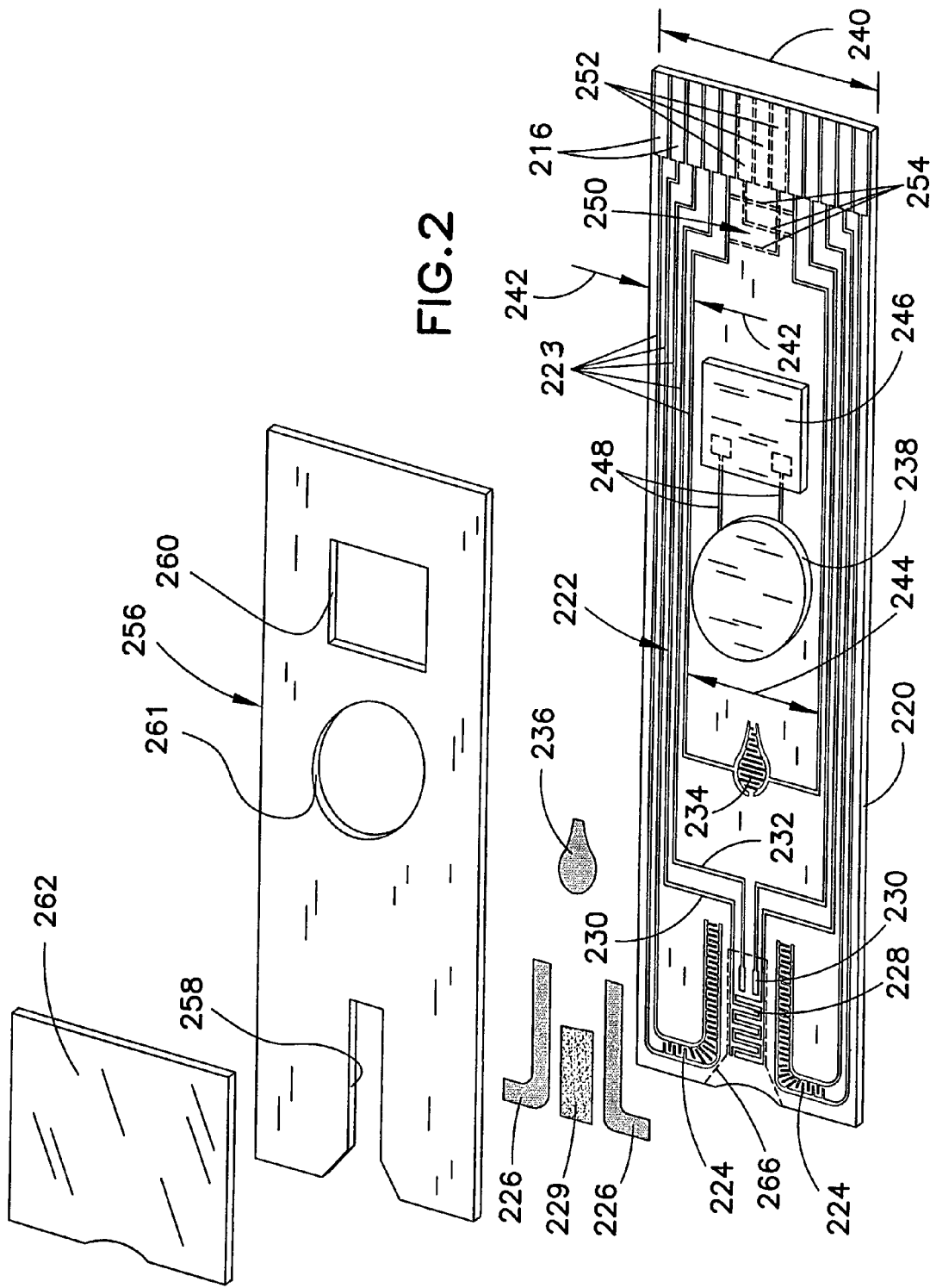
FIG. 2 is an exploded perspective view of the biosensor of FIG. 1.

With further reference to FIGS. 1 and 2, strip 200 is generally of a laminar structure and includes three primary layers. The base substrate layer 220 is generally a flexible polymeric material such as polyester, especially high temperature polyester materials; polyethylene naphthalate (PEN); and polyimide, or mixtures of two or more of these. A particularly preferred base substrate material is a 10 mil thick MELINEX® 329 layer available from duPont. Substrate 220 is initially coated with a conductive material such as a 50 nm layer of gold, and the complex electrical pattern 222 can be then formed therefrom by broad field laser ablation. The broad field laser ablation method is described in the METHOD OF MAKING A BIOSENSOR application incorporated above. Materials for the specific biosensor layers and the method of assembling those materials is described in the Slot Vent Opening application, also incorporated above.

The electrical pattern 222 includes contacts or contact pads 216, which, as described above, can be electrically linked to an instrument that reads strip 200. Traces 223 run lengthwise along strip 200 and are typically used to connect electrical devices to the contact pads 216 or to connect two or more electrical devices on or in strip 200 together. For example, substrate 220 includes a measuring electrode set 228 coated by a reagent 229 and a sample sufficiency electrode set 230, the operation of which are described in detail in the Dose Sufficiency, Slot Vent Opening, and DEVICES AND METHODS RELATING TO ELECTROCHEMICAL BIOSENSORS applications, all of which were incorporated by reference above. These electrode sets are connected to their respective contact pads by traces 230 and 232 and in turn through traces 223 as shown.

User interface devices comprising L-shaped micro-electrode arrays 224 are formed on base substrate 220 and are coated with organic light emitting diodes ("OLEDs") 226, which illuminate upon a voltage being provided across arrays 224. The voltage is applied or removed upon or after the occurrence of a triggering event, as described in more detail below. Similarly, micro-electrode set 234 formed on substrate 220 is coated with a second OLED 236 that illuminates or turns off upon the occurrence of the same or a different triggering event, as is also described in more detail below.

A power generator 238 is provided on strip 200 and can be used to power various other electrical devices present on the strip, as explained below. Many suitable power generators are commercially available and can be employed as power generator 238, but power generator 238 should preferably be formed as a small and especially thin material so as not to significantly increase the thickness of test strip 200.

Test strip 200 includes digital device 246, which is shown in FIG. 2 wired to power generator 238 by traces 248. Digital device 246 may be an integrated circuit, an RFID tag or other digital device, as described in more detail below. Further, a portion of the electrical pattern may comprise a digital device 250, as explained in more detail below.

Laminated to base substrate 220 is a spacer layer 256, formed, e.g., from a 4 or 5 mil thick Melinex® 329, 339 or 453 material available from DuPont Teijin Films. In certain embodiments, particularly those including light emitters such as OLEDs 226 and 236, it is preferable that the spacer layer material be clear or translucent so that the OLEDs are visible when lit. The Melinex® 453 material works well for this purpose. Spacer layer 256 forms a void 258 that defines the height and perimeter of the sample receiving chamber 218 (FIG. 1). The precise volume of the sample receiving chamber is defined in the Slot Vent Opening application, which was incorporated above. Spacer layer 256 also includes "cut-outs" 260 and 261 that are sized to receive digital device 246 and power generator 238, respectively. These devices will typically be thicker than the spacer layer, such that they may protrude slightly from the top of strip 200 as shown in FIG. 1.

A covering layer 262 overlies and is laminated to spacer layer 256. Covering layer 262 is also preferably made from a transparent Melinex® film that is about 4-5 mils thick. Covering layer 262 overlies most of void 258 and forms the ceiling or top boundary for sample receiving camber 218. The cover terminates short of the full length of void 258 and thereby forms a vent opening 264 as shown. Vent 264 allows air to be displaced from chamber 218 as fluid sample enters it. As can be appreciated with respect to FIG. 1, OLED coatings 226 and 236 are visible when lit through the covering and spacer layers.

Optionally, to reduce the extent to which devices 238 and 246 protrude from strip 200, cover layer 262 may extend further toward meter insertion end 214, such that it is coextensive with layer 256. The cover 262 would then be formed with a hole overlying the void 258 to form the vent. Alternatively, the cover could be formed in two pieces forming a gap therebetween, as described in the Slot Vent Opening application, incorporated by reference above. This longer spacer layer may also include cut-outs that align with cutouts 260 and 261 and reduce the extent to which devices 238 and 246 protrude from strip 200. Typically, however, it is preferable for electrical devices in the user interface or power generation zones to be sufficiently thin such that they can be covered by covering layer 262 for protection from electromagnetic interference.

Electrical Pattern.

The electrical patterns for use with embodiments incorporating the present invention are typically formed by broad field laser ablation, which is described in detail in the METHOD OF MAKING A BIOSENSOR application that was incorporated by reference above. This method allows several electrical functionalities to be located within and outside of measurement zone 202—with room to spare on an already very small test strip. For example, arrow 240 in FIG. 2 represents the approximate width of strip 200, which is about 9 mm in the illustrated embodiment. The strip illustrated in FIGS. 1 and 2 is preferably about 33-38 mm in length. Arrows 242 illustrate the distance from the edge of the strip to the innermost trace 223, and this width can be configured to be about 1 mm or even as small as about 0.2 mm. Remarkably, this means that width 244, which is the width available for components such as power generator 238 and digital device 246, can be about 8 mm or more for a 9 mm wide strip having ten electrical traces running lengthwise along it. One of ordinary skill should readily appreciate that the electrical patterns embodied by the present invention, while complex, can nonetheless be advantageously configured into a relatively small space, such that ample room remains for other devices having relatively large footprints to be placed on the strip.

Measurement Zone.

Generally, the measurement zone incorporating the present invention can vary widely insofar as the type and quantity of functionalities provided therein. Turning to FIGS. 1 and 2, the measurement zone 202 includes a sample receiving chamber 218 whose periphery is approximately indicated in FIG. 2 by dashed line 266. (As indicated above, the precise volume of the sample receiving chambers of various embodiments disclosed in this application can be determined with reference to the Slot Vent Opening application, incorporated by reference above.) Macro-electrode array 228 includes a working electrode and a counter electrode, each having one or more interdigitated fingers as shown. Electrode set 228 estimates the concentration of analyte based upon the reaction of the analyte with the reagent 229 coated on the electrode set. Once a sufficient sample has entered chamber 218, a suitable potential or series of potentials across the working and counter electrodes are applied, and the impedance or other characteristic is measured and correlated to the concentration of analyte. Measuring electrodes of this type and reagent suitable for reagent layer 229 are described in the Slot Vent Opening and DEVICES AND METHODS RELATING TO ELECTROCHEMICAL BIOSENSORS applications incorporated above, and need not be described in further detail herein.

As mentioned, the voltage or potential is preferably not applied across electrode set 228 until the sample chamber has filled with the requisite volume of sample. In this connection, sample sufficiency electrode set 230 is provided at a downstream location in chamber 218. When fluid has wetted electrode set 230, its resistance or impedance (which can be intermittently monitored by applying a voltage to the contact pads 216 connected to electrode set 230) will drop, thereby indicating sample has reached the interior end of the chamber and sufficient sample has thus been received. A potential or series of potentials can thereafter be driven across electrode set 228 to perform the measurement. Sample sufficiency electrodes suitable for use with the present invention are disclosed in the Dose Sufficiency application that was incorporated by reference above. Additionally, once the sample sufficiency electrodes indicate that sufficient sample has been received, they can be used for other measurements, as also disclosed in the Dose Sufficiency application. It should also be understood that a single sample sufficiency electrode could be used and a voltage applied across it and one of the measurement electrodes for testing.

Figure 3:
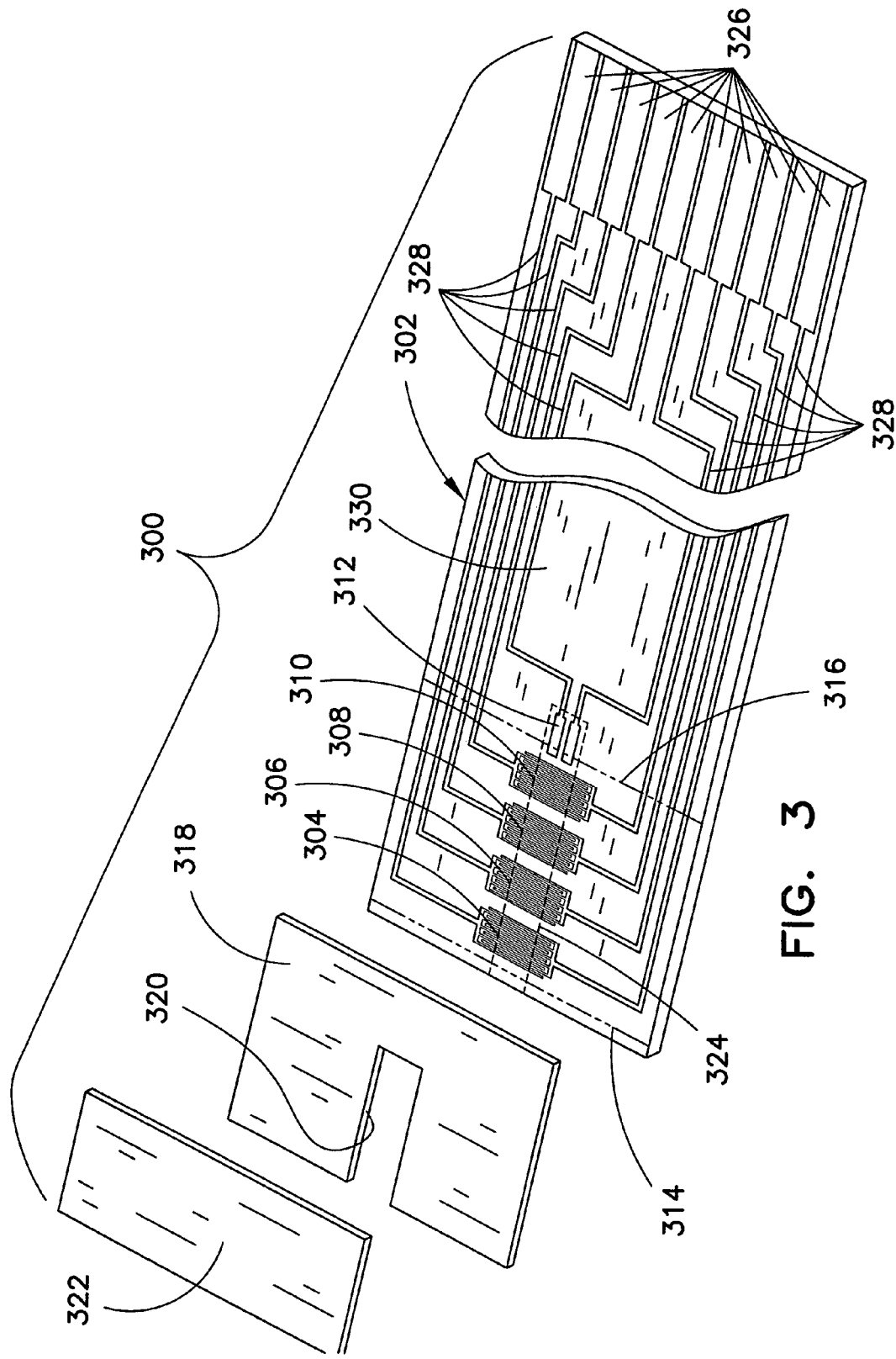
FIG. 3 is an exploded perspective view of a biosensor in accordance with a second embodiment of the present invention.

Turning now to FIG. 3, a test strip 300 is shown with a sample receiving chamber having multiple, redundant functionalities. Strip 300 includes base substrate 302, four sets of micro-electrodes 304, 306, 308 and 310, and a set of sample sufficiency electrodes 312 formed thereon. A reagent layer whose edges are indicated by dashed lines 314 and 316 is coated onto the micro-electrode sets. Strip 300 also includes a spacing layer 318 having a void section 320, which, in cooperation with covering layer 322 and base substrate 302, partially defines the boundaries of the sample receiving chamber. The position of the sample receiving chamber is generally indicated by dashed line 324 on substrate 302, although the void portion beneath the vent is not part of the sample receiving chamber. The micro-electrode sets and sample sufficiency electrodes are electrically connected to contact pads 326 through traces 328. The architecture just described is essentially the same as that described with reference to FIG. 1-2, the difference being the electrical devices contained in the sample receiving chamber. Advantageously, a large central portion 330 of the base substrate 302 is not occupied by the electrical pattern and would be available to add additional user interface, power, or digital devices, as described elsewhere herein.

In the embodiment shown in FIG. 3, identical microelectrodes are provided to make identical measurements. Sample fluid enters the sample receiving chamber 324 and is drawn in by capillary action past each of the micro-electrode arrays until it wets sample sufficiency electrode set 312, whereupon potentials are applied across each of the microelectrode arrays 304, 306, 308 and 310. The circuitry in the instrument (not shown) that reads the strips drives a potential across each electrode set through contacts 326 and traces 328. Alternatively, electrodes sets 304, 306, 308 and 310 could be wired in parallel (not shown), in which case a single pair of contact pads would connect all four electrode sets to the meter. In this case, the parallel configuration of the four sets would provide an "on strip" average for the value being measured by the four electrode sets.

Even though it contains five electrode sets, sample receiving chamber 324 nonetheless has a very small volume, on the order of less than about 500 nl.

Figure 4:
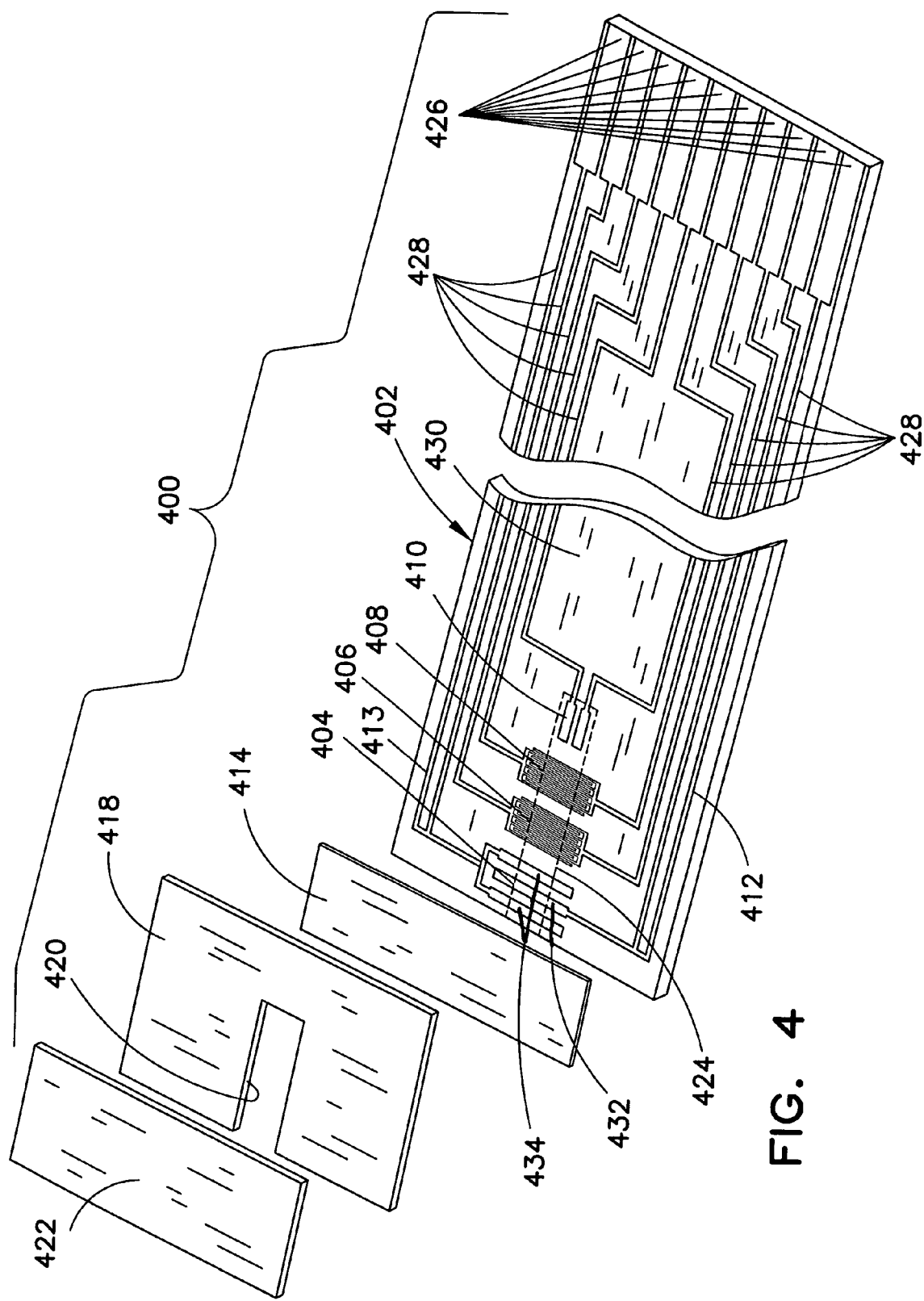
FIG. 4 is an exploded perspective view of a biosensor in accordance with a third embodiment of the present invention.

Turning now to FIG. 4, a test strip 400 is shown having a measurement zone with multiple, different functionalities. Strip 400 includes base substrate 402 with four sets of electrodes 404, 406, 408 and 410, and a set of fault detect electrode traces 412 and 413 formed thereon. A reagent stripe 414 is coated onto electrode set 404 and micro-electrode set 406 in this embodiment. Strip 400 also includes a spacing layer 418 having a void section 420, which, in cooperation with covering layer 422 and base substrate 402, defines the boundaries of the sample receiving chamber. The position of the sample receiving chamber is indicated generally by dashed line 424 on substrate 402. The electrode sets and sample sufficiency electrodes are electrically connected to contact pads 426 through traces 428. The architecture just described is essentially the same as that described with reference to FIG. 2, the difference being the electrical devices contained in the measurement zone. Again, a large central portion 430 of the base substrate 402 is not occupied by the electrical pattern and would be available to add additional user interface, power, or digital devices, as described elsewhere herein.

In the embodiment shown in FIG. 4, The first electrode pair 404 encountered by the sample includes working electrode 432, a single-finger electrode. First electrode pair 404 also includes counter electrode pair 434, a two-finger electrode, with one finger on either side of working electrode 432. Each finger in first electrode pair 434 is about 250μm wide, and a gap of about 250 μm separates each counter electrode finger from the working electrode finger. The system driver connects to contacts 426 to use the first electrode pair 404 to obtain an estimated concentration of analyte in the sample.

The second electrode pair 406 comprises two electrodes of five fingers each. These fingers are each about 50 μm wide with a separation of about 30 μm between them. Each electrode in the second pair connects to a conductive trace 428 to be electrically connected to a contact 426, which contacts are used to drive and measure for a first correction factor such as hematocrit based on the analyte interaction with the second pair of electrodes.

The third electrode pair 408 is also a micro-electrode configuration, with each of the two electrodes in the third pair 408 having five fingers interdigitated with the five in the other electrode. Each finger is again about 50 μm wide, with a gap of about 30 μm between them. Each electrode in the third pair 408 is connected via a conductive trace 428 to a contact 426, which contacts are used to drive and measure for a second correction factor such as temperature based on the analyte interaction with the second pair of electrodes.

The fourth set of electrodes comprises sample sufficiency electrodes 410 that signal when the sample has filled the chamber such that electrode sets 404, 406 and 408 can then be driven to perform their respective measurement functions.

The fifth functionality in the measurement zone of strip 400 relates to fault detect traces 412 and 413 for electrode set 404. Trace 413 connects to counter electrode 434 and is used to correct variant voltage across the pair, whereas fault detect trace 412 on working electrode 432 compensates for measured current. Additionally, traces 412 and 413 can be used to apply a potential between the primary traces and the fault detect traces to determine whether there are any defects in the primary traces. This fault detection feature is fully described in the Quality Assurance application that was incorporated by reference above.

Even with five electrical devices or functionalities provided in the measurement zone, the sample receiving chamber 424 nonetheless has a very small volume, on the order of less than about 500 nl.

Figure 5:
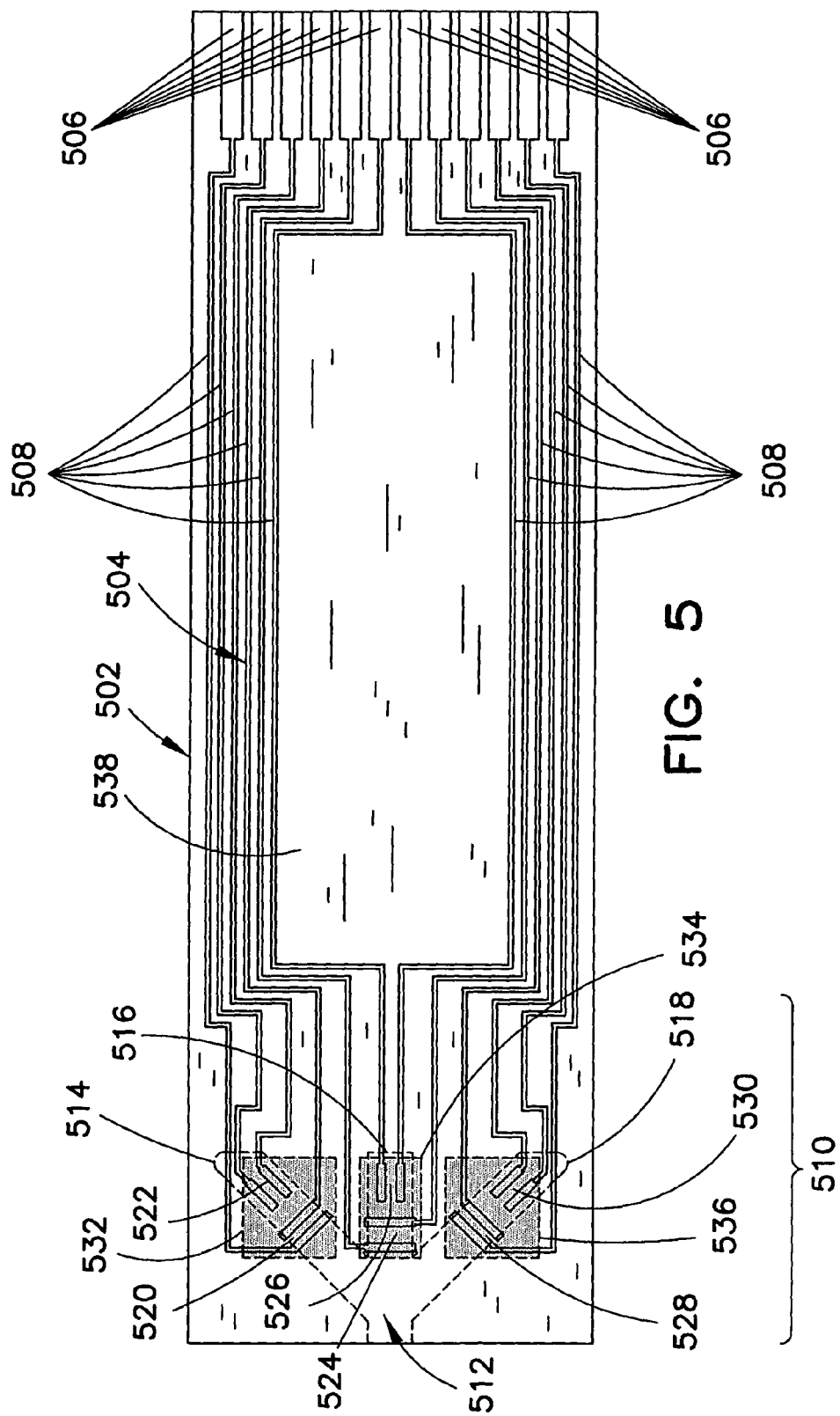
FIG. 5 is a plan view of a base substrate of a biosensor in accordance with a fourth embodiment of the present invention.

Turning now to FIG. 5, a base substrate 502 for a test strip of the type described above is shown. Substrate 502 includes an electrical pattern 504 formed thereon having contact pads 506 and traces 508 leading to the electrode sets disposed in the measurement zone 510. Measurement zone 510 includes a sample receiving chamber 512 having three branches or prongs 514, 516 and 518. Branch 514 includes electrode sets 520 and 522, branch 516 includes electrode sets 524 and 526, and branch 518 includes electrode sets 528 and 530. A reagent layer 532 covers electrode sets 520 and 522, a reagent layer 534 covers electrode sets 524 and 526, and a reagent layer 536 covers electrode set 528 and 530. A spacing layer (not shown in FIG. 5) as described above is formed with voids corresponding to and defining the branched sample receiving chamber, and a covering layer overlies the spacing layer. Vent holes are formed in the covering layer to allow air to escape each of the branches of the sample receiving chamber.

One advantage of the system shown in FIG. 5 is that it allows multiple analytes to be tested in a single test strip. For example, reagent layers 532, 534 and 536 can be comprised of three different reagents for testing three different analytes, e.g., a lipid panel that tests total cholesterol, HDL cholesterol and triglycerides. Reagents with appropriate enzymes and mediators for these analytes are disclosed in the Reagent Stripes application that was incorporated by reference above. Alternatively, all three reagents can be identical, in which case three of the same tests can be performed in parallel, such that each branch of the sample receiving chamber effectively receives its own fresh supply of fluid sample. By contrast, a series of electrode sets in a single-branched chamber poses the potential of contamination to the downstream electrode sets.

As with the embodiments illustrated above, it should be appreciated that a large portion 538 is available in the middle of substrate 502 and could be configured to support additional electrical devices.

Power Generation

Returning now to FIGS. 1 and 2, a power generator 238 is positioned centrally on strip 200. The power generator 238 may comprise a battery such as a commercially available custom made Power Paper brand energy cell, available from Power Paper, Ltd., Kibbutz, Israel. These cells are preferably printed on a very thin substrate such as paper or thin polymer. By means of basic screen-printing techniques, different layers of conductive inks are printed to form the various components of cell 238, which are then laminated together and in turn laminated to substrate 220. In the embodiment illustrated in FIG. 2, battery 238 has a diameter of about 5.3 mm and a thickness of less than about 0.5 mm. Battery 238 is mounted to substrate 220 by ordinary adhesives or other suitable means and connects to leads 248 as show, preferably by conductive epoxy. Battery 238 produces 2.7-3.1 Volts, a current of 4-5 mA and has an "on time" of between 5-90 seconds. These parameters are sufficient for powering one of the inventive OLED circuits described below, a traditional LED, or a small piezoelectric device which produces sound, or any number of similar devices. In view of the teachings herein, which minimize the footprint of even complex electrode patterns, two or more such batteries 238 could be positioned on strip 200 and wired together to increase power production.

Other power generators 238 could be substituted for the battery just described. For example, if only a short burst of energy is needed, for example to light a diode or produce a short audible sound, a super capacitor or ultra-cap modified to have a very slim profile could be used as power generator 238. In use, for example, in one embodiment, strip 200 would be inserted into the instrument (not shown) for strip identification, strip integrity checks, temperature determination, and charging the capacitor or other power storage element. The self-powered strip is then removed from the instrument, placed at the dose site, and returned to the instrument for measurement computation and display.

In view of the teachings herein, one of skill in the art would readily recognize other power generators that could be employed as power generator 238. It is preferable, however, that the power generator be as thin as possible so as not to significantly increase the thickness of the test strip.

Digital Devices.

Still referring to FIGS. 1 and 2, a digital device 246 is positioned adjacent power generator 238 and is wired thereto by traces 248. Device 246 could be a radio frequency identification ("RFID") tag. RFID 246 is preferably less than about 1 mm thick, more preferably less than 0.5 mm thick, and has a width of less than about 7 mm. In one embodiment, device 246 contains digital calibration data concerning the test strip and can communicate such data to an RFID reader (not shown) that is included in the instrument (not shown). Most commercially available RFID's are typically "passive," i.e., they are powered by the radio signal emanating from the reader that reads them. Thus, if device 246 is an RFID, it need not be wired to a power generator such as power generator 238. RFID technology is known in the art and the details thereof need not be described any further herein.

As noted above, digital device 246 could be provided as an on-board integrated circuit with computing power, powered by battery 238 and connected thereto by traces 248. Two commercially available examples include Texas Instruments MSP430C11 and MicroChip PIC 12F675 integrated low power micro-controllers for governing sample acquisition and rudimentary measurements to support dosing the strip without the strip being inserted in the meter. As yet another option, device 246 could be provided in the form of a conventional wired storage device such as a MicroChip 24AA01 1K bit serial EEPROM, in which event it would include data such as lot code, calibration data and the like.

As shown in FIG. 2, strip 200 also includes a digital device 250 which is comprised of a combination of contact pads 252 and conductive links 254 of electrical pattern 222. Contact pads 252 and conductive links 254 are shown in phantom because any one (or all) of them may or may not be present in the finished test strip, depending upon the information that is to be encoded onto the test strip. Each link or contact pad can be thought of as a binary switch having a value of 0 (if not present) or 1 (if present). Any given configuration of absent/present links and contact pads may include digital information concerning lot code, expiration date, type of analyte the strip is intended to analyze and so forth. A detailed enabling description of digital device 250 is disclosed in the Coding Information application that was incorporated by reference above.

Optionally, a photodiode sensor could be mounted on the test strip in the digital device zone or elsewhere to detect an environmental condition such as ambient light. The meter could then apply a voltage to the micro-electrode arrays such as micro-electrode arrays 224 so that they illuminate the measurement zone. One of skill in the art should thus appreciate that the term "digital device" for purposes of this application is somewhat broader than its common usage in the art, in that it includes devices such as a photodiode or similar devices that may be provided in the digital zone.

User Interface Devices.

As briefly described earlier, the test strip 200 shown in FIGS. 1 and 2 includes a user interface zone 204 that includes OLEDs coated onto micro-electrode arrays. Specifically, with reference to FIG. 2, OLEDs 226 are coated onto micro-electrodes 224 and OLED 236 is coated onto micro-electrode array 234.

Electrode arrays 224 are wired through traces 223 to contact pads 216. Thus, a "triggering event" occurs when strip 200 is inserted into a meter (not shown), upon which event the circuitry of the meter recognizes that a strip has been inserted and produces a voltage across electrode sets 224. In turn, the coatings 226 illuminate. If the strip 200 is being used in conditions of dim lighting, the OLED coating advantageously illuminates the sample receiving chamber 218 so that the user can visually confirm that the fluid sample is contacting the correct part of the strip 200 and that the sample fluid is being drawn into the strip. As noted above, the spacer and covering layers forming test strip 200 are preferably transparent or translucent such that the light emitted from the OLEDs is visible through them.

OLED 236 can be configured to illuminate (or turn off) upon sufficient sample being received in the sample receiving chamber. Sample sufficiency electrodes 230 are wired through traces 223 to contact pads 216 and in turn to the meter (not shown) that reads the strips. Once the meter detects from electrodes 230 that the chamber is filled with the requisite size sample, the meter can apply a voltage across electrode set 234 through the appropriate contact pads 216 and traces 223.

OLED 236 will then illuminate, thereby providing the user a positive visual indication that the chamber has been properly filled.

Figure 6:
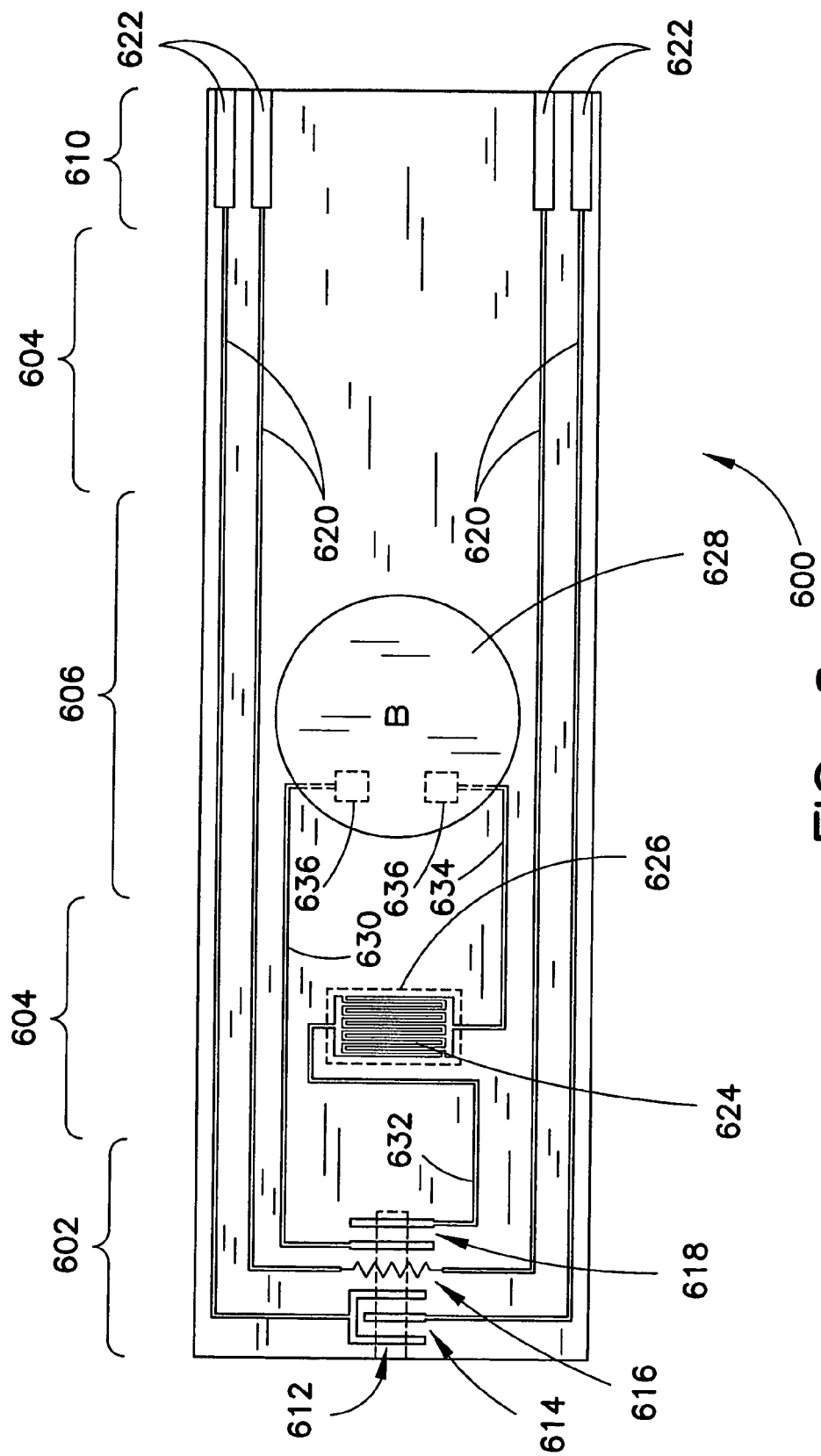
FIG. 6 is a plan view of a base substrate of a biosensor in accordance with a fifth embodiment of the present invention.

FIG. 6 shows a base substrate 600 of another test strip embodiment incorporated by the present invention. The test strip has a measurement zone 602, two user interface zones 604 and 604', a power generation zone 606, and a meter connection zone 610. This embodiment illustrates the point alluded to above, viz., that the locations of various "zones" of a particular test strip embodying the principles of the present invention may overlap, or in the case of the embodiment illustrated in FIG. 6, may be discontinuous or bifurcated.

The sample receiving chamber 612 includes three different electrical devices or functionalities: a measurement electrode set 614, a thermistor 616 and a sample sufficiency electrode set 618. Electrode set 614 is connected to traces 620, which terminate in contact pads 622 disposed at meter connection zone 610 of the strip. The sample sufficiency electrode set 618 is part of a circuit which includes a micro-electrode array 624 having an OLED 626 coated thereon and a battery 628. Electrical devices 618, 624 and 628 are wired in series by traces 630, 632 and 634. Traces 630 and 634 terminate in the power generation zone 606 with contact pads 636 (shown in phantom) to which the battery 628 is connected. The second or bifurcated user interface zone 604' includes a traditional diode 638 wired by traces 620 to contact pads 622.

In use, the strip is dosed with a sample that is drawn into chamber 612 by capillary action. In the embodiments described above, the sample sufficiency electrodes were adapted to be driven by circuitry from a meter to which the strip is inserted. The embodiment in FIG. 6, however, employs a different approach. In this embodiment, sample sufficiency electrode set 618 acts as a switch in the circuit containing electrodes 618, electrode array 624 and battery 628. Battery 628 is a Power Paper type battery as described above that produces 2.7-3.1 Volts and a current of 4-5 mA for about 5-90 seconds. Once the aqueous fluid sample saturates sample sufficiency electrodes 618, the circuit closes. If blood is the sample fluid, the ionic strength thereof should be sufficient to close the circuit. However, one skilled in the art would readily recognize numerous coatings that could be applied and dried onto electrode set 618 to ensure sufficient current transfer upon wetting with other fluid samples. In any event, closing the circuit is a triggering event which results in a voltage being produced across micro-electrode array 624, which in turn causes OLED layer 626 to illuminate. In this manner, the illumination of OLED 626 provides a positive visual verification to the user that the sample chamber has been filled. Electrical device 616 is a thermistor that is used to measure the temperature of the sample receiving chamber. One thermistor suitable for device 616 is surface mount thermistor available from Vishay Intertechnology, Inc., Layern, Pa., part no. NTHS-0402N01N100KJ. Thermistor 618 is driven by electrical circuitry from a meter (not shown) through contacts 622 and traces 620. If the temperature of the sample receiving chamber is not within a desired range for testing, the meter circuitry can apply a voltage to conventional LED 638 through contacts 622 and traces 620 to cause it to illuminate. This signals the user that the temperature of the sample is outside of a preferred range, in which event the user may then possibly repeat the test under better conditions. An LED that is suitable for mounting on substrate 600 is available from Stanley Electrical Sales of America, Inc., part no. PY1114CK. This LED is mounted to base substrate 600 preferably by a conductive epoxy. Optionally, instead of an LED, user interface zone 604' may include a signal producing device that produces sound, such as a piezoelectric available from U.S. Electronics, Inc., St. Louis Mo., part number USE14240ST.

Figure 7:
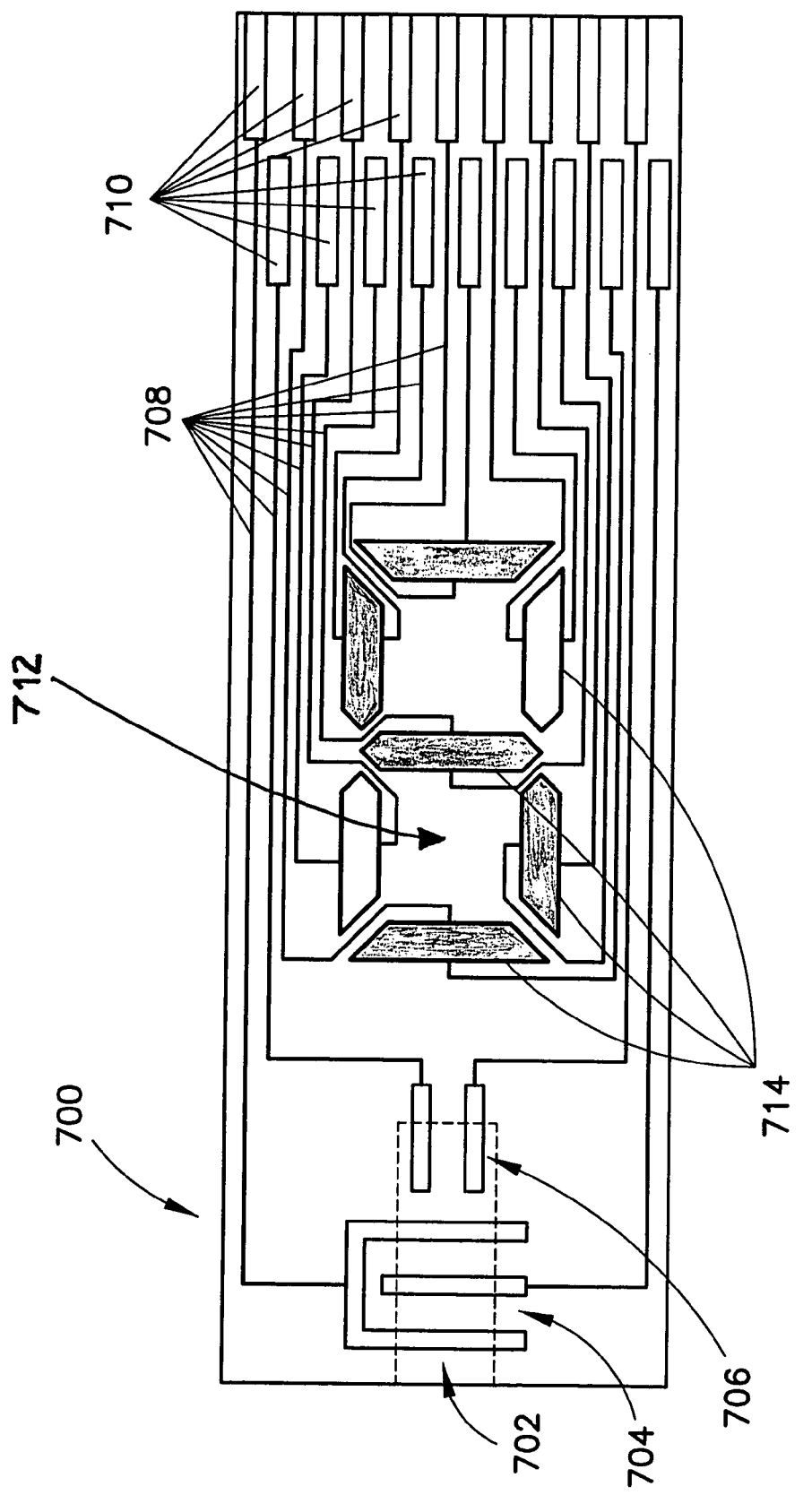
FIG. 7 is a plan view of a base substrate of a biosensor in accordance with a sixth embodiment of the present invention.

Turning now to FIG. 7, a test strip with yet another innovative electrically driven signal generator is illustrated. Base substrate 700 of the test strip includes a measurement zone that includes a sample fluid receiving chamber 702 having disposed at least partially therein a measurement electrode set 704 and sample sufficiency electrode set 706, whose functionality and operation are described above. Suitable spacing and covering layers (not illustrated in FIG. 7) cover substrate 700 to form a test strip, as described above and in the Slot Vent Opening application incorporated by reference above. Substrate 700 includes a numerical display 712 comprised of individual segments 714 that have a shape not unlike that of the segments used for traditional LED or LCD displays. The layer or layers of the test strip (not shown) that cover display 712 are translucent or transparent such that display 712 is visible therethrough. Segments 714 include an OLED coating like that described above overlying a micro-electrode IDA, as also described above (but not shown in FIG. 7). Each segment 714 has two electrodes (not shown) having two traces 708 extending therefrom and leading to respective contact pads 710. Voltages can be applied across selective ones of the contact pads 710 to illuminate display 712 to produce any of the digits 0 to 9, a "5" being shown illuminated in FIG. 7.

Optionally, additional digits and associated contact pads and traces can be provided with display 712 on substrate 700. The design of the test strip with this numerical display should balance (1) the desire to keep the strips small, (2) the need to make the display large enough to be read by even those users with impaired vision, and (3) the space required from substrate 700 to accommodate the traces, contact pads, and digits. A test strip having a base substrate 700 as shown in FIG. 7 with one digit has a length of about 33-38 mm, a width of less than about 15 mm, preferably about 9 mm, and a thickness of less than about 1 mm. The other layers that are laminated to substrate 700 can be configured and assembled in accordance with the Slot Vent Opening application, incorporated by reference above. It should be appreciated that the micro-electrode arrays and OLEDs coating them (to form segments 714 of display 712) do not increase the thickness of the strip.

In use, the test strip having substrate 700 is inserted into a meter (not shown), a fluid sample is provided to sample receiving chamber 702, and the meter calculates the numerical estimate of analyte concentration. Thereupon, the circuitry in the meter drives voltages across selective ones of the contact pads 710 to illuminate a number on display 712 that corresponds to the estimate of analyte concentration. If only one digit were provided in display 712 as shown in FIG. 7, and the analyte whose concentration is being estimated were glucose from a blood sample, the single digits could be assigned a range. For example, a "0" might correspond to a 50-100 mg/dl concentration of glucose, a "1" to 100-150 mg/dl, a 2 to 150-200 mg/dl and so on. If two digits were provided in display 712, then the display could simply show the first two digits of the result. In such case a "10" displayed would mean 100-109 mg/dl, a "21" would mean 210-219 mg/dl, etc.

Alternatively, the analyte concentration might be displayed by sequentially displaying digits. For example, "126" mg/dL might be displayed as a "1" followed by a "2", followed by a "6", and the sequence terminated with a unique symbol to indicate completion and avoid user confusion. In this manner, a three-digit whole number can be conveyed to the user with a single digit display.

With three digits, a whole number for mg/dl concentration can be displayed all at once, as is typically done with traditional glucose meters.

While FIG. 7 embodies an electrochemical test strip, it should be understood that the innovative on-board display could be provided on test strips which employ other measurement techniques, e.g., photometric principles.

Forming the test strips or biosensors as flattened articles offers several advantages, especially in terms of storing and dispensing, as described in the Dispenser application incorporated above, but it is expected that one skilled in the art can apply the teachings herein to other test devices. The inventive display as well as other features described above may be employed in other test devices that have, e.g., a cylindrical body. Examples of these other test devices include environmental, food testing and other such testing devices. Even biosensors incorporating the inventive features described herein, while generally comprising a flat and thin shape, may have portions thereof that are sized and shaped to accommodate various electrical devices, as described above.

OLED Working Examples.

Polymer light-emitting devices are typically configured as a thin film (e.g., about 0.1 microns of a polymer such as polyparaphenylene vinylene) sandwiched between two different metallic electrodes. The anode is transparent and lies on a transparent substrate. The typical combination is indium tin oxide on glass. The experiments below, however, employ a light emitting polymer coated onto a micro-electrode interdigitated array (IDA) in which the electrodes are co-planar.

EXAMPLE I

To preparing the coating, 0.012 g of tris (2,2'-bipyridyl) dichlororuthenium (II) hexahydrate (CAS Registry No. 50525-27-4) was combined with 1 ml of acetonitrile. The compound did not completely dissolve. Deionized water was then added dropwise until the ruthenium compound completely dissolved.

Two functional interdigitated micro-electrode arrays (IDAs) were used. The IDAs had 750 pairs of interdigitated fingers with each finger having a width of 2 μm, a length of 6 mm, and a spacing between the next closest finger (i.e., gap width) of about 2 μm. The IDAs were custom fabricated on a silicon wafer by Premitec Inc., Raleigh, N.C. The IDAs were each coated with 20 l of the solution just described. The coated IDAs were then placed in a desiccator and allowed to dry. The reagent coatings did not dry uniformly and had a ridge around the circumference of the coating.

Using a BAS 100 W electrochemical potentiostat, a 3 volt potential was applied across the micro-electrode arrays, whereupon light was emitted from the coatings. Both electrodes were tested several times with light being emitted from the coating on application of about 3 volts. A Keithley 236 "Source Measure Unit" was than setup as a better voltage source for future measurements.

EXAMPLE II

In order to obtain a better coating than that obtained in Example I, a solution of 1% PVP 25k (BASF) was prepared in deionized water. The ruthenium compound used in Example I was then mixed with the PVP solution in a 1:1 ratio and the resulting solution was applied to several additional IDAs. The first IDA had a spacing between the interdigitated fingers of approximately 2μ/m as described above and the other had a finger spacing of approximately 21μm and 50 finger pairs. This second IDA had a finger width of 21μm, a finger length of 6 mm and was formed on a Upilex substrate also custom fabricated by Premitec. The coating composition containing the PVP produced a uniform coating on both types of IDA's.

Using the Keithley SMU-236, a three (3) volt potential was applied across the IDA with the 21μm finger spacing, but this voltage was not sufficient to cause the OLED to illuminate. Three (3) volts was also applied across the IDA with the 2 μm finger spacing, which caused the OLED to illuminate with good intensity. Increasing the voltage on the 2 μm IDA increased the intensity. Voltages of about 10-20V were required to produce reasonable intensities in the IDA with the 21 μm gap width between the fingers.

EXAMPLE III

The electrodes used in the preceding examples were left at room temperature and humidity and the experiments described above repeated at approximately 1-2 month intervals. The OLEDs still illuminated with the same voltages used in the previous examples.

Other OLEDs.

It is anticipated that substituting other polymers in the OLED matrix used in the experiments above may improve the results, in terms of the voltage required to illuminate and the overall intensity achieved with a given voltage. One such compound is Poly(styrenesulfonate)/poly(2,3-dihydrothieno (3,4b)-1,4-dioxin), available from Aldrich. Other Poly(sodium, 4-styrenesulfonate) compounds may also perform well or better than the polymer used in the above examples. One of skill in the art would recognize that many other known light emitting compounds may work suitable as OLEDs for use in the biosensors disclosed herein.

While a preferred embodiment incorporating the principles of the present invention has been disclosed hereinabove, the present invention is not limited to the disclosed embodiments. Instead, as noted above, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biosensor for analyzing a fluid sample, comprising:

a test strip;

the test strip defining a measurement zone having a sample receiving chamber in which is disposed a measurement electrode for detecting the presence or concentration of an analyte in the fluid sample, the sample receiving chamber including a reagent which reacts with the fluid sample, the test strip including a dosing edge wherein the sample receiving chamber is open at the dosing edge to receive the fluid sample;

the test strip further defining a user interface zone in which is disposed an electrically driven signal generator which emits a visible, audible or tactile signal upon occurrence of a triggering event, further wherein the signal generator comprises a light disposed proximate the sample receiving chamber, the light illuminating the sample receiving chamber upon the occurrence of the triggering event; and the test strip including a meter insertion end having contacts thereon that are adapted to electrically connect to a test meter.

2. The biosensor of claim 1, wherein the signal generator comprises a numerical display corresponding to the concentration of an analyte in the fluid sample.

3. The biosensor of claim 1, wherein the signal comprises sound.

4. The biosensor of claim 1, wherein the signal generator comprises an OLED.

5. The biosensor of claim 4, further comprising a micro-electrode set disposed on a substantially planar surface of the test strip, the OLED being coated onto the micro-electrode set.

6. The biosensor of claim 1, wherein the signal generator comprises an LED.

7. The biosensor of claim 1, wherein the signal generator comprises a piezoelectric wafer, wherein the signal is audible.

8. The biosensor of claim 1, wherein the test strip further comprises a digital information zone in which is disposed a digital device.

9. The biosensor of claim 8, wherein the digital device comprises an electrical pattern encoded with at least one parameter about the biosensor.

10. The biosensor of claim 8, wherein the digital device comprises an integrated circuit.

11. The biosensor of claim 8, wherein the digital device comprises an RFID tag.

12. The biosensor of claim 8, wherein the digital device is encoded with the type of analyte the biosensor is configured to analyze.

13. The biosensor of claim 8, wherein the digital device is encoded with at least one of a lot code and an expiration date of the biosensor.

14. The biosensor of claim 1, wherein the test strip further defines a power generating zone in which is disposed a power generator.

15. The biosensor of claim 14, wherein the power generator is electrically connected to the signal generator and provides power thereto upon the occurrence of the triggering event.

16. The biosensor of claim 14, wherein the power generator comprises a battery.

17. The biosensor of claim 16, wherein the battery comprises a thin film.

18. The biosensor of claim 14, wherein the power generator comprises a capacitor that discharges upon the occurrence of the triggering event.

19. The biosensor of claim 14, wherein the power generator generates at least 2 volts for at least 2 seconds upon the occurrence of the triggering event.

20. The biosensor of claim 1, wherein the measurement zone comprises a dose sufficiency electrode.

21. The biosensor of claim 1, further comprising:
a first set of electrodes at least partially disposed in the sample receiving chamber for estimating the concentration of an analyte in the sample, the first set of electrodes including the measurement electrode; and
a second set of electrodes at least partially disposed in the sample receiving chamber.

22. The biosensor of claim 21, wherein the second set of electrodes comprises a pair of electrodes with substantially parallel, interdigitated fingers, each electrode having at least two fingers.

23. The biosensor of claim 1, wherein the sample receiving chamber has a volume of less than about 250 nl.

24. The biosensor of claim 1, wherein the sample receiving chamber has a volume of less than about 100 nl.

25. The biosensor of claim 1, wherein the reagent covers the measurement electrode.

26. A biosensor for analyzing a fluid sample, comprising:
a test strip;
a measurement zone disposed in or on the test strip, the measurement zone defining a sample receiving chamber in which the fluid sample is received and analyzed;
a power generator disposed in or on the test strip;
a user interface zone disposed in or on the test strip, the user interface zone having an electrically driven signal generator which emits a signal upon occurrence of a triggering event, the signal generator includes a light disposed proximate the sample receiving chamber, the light illuminating the sample receiving chamber upon the occurrence of the triggering event;
the test strip having a meter insertion end that is adapted to electrically connect to a test meter; and
the test strip having a dosing edge wherein the sample receiving chamber is open at the dosing edge to receive the fluid sample.

27. The biosensor of claim 26, wherein the power generator comprises a battery.

28. The biosensor of claim 27, wherein the test strip defines a substantially planar substrate and the battery comprises a thin film adhered to the substrate.

29. The biosensor of claim 26, wherein the power generator comprises a capacitor.

30. The biosensor of claim 26, wherein a sample sufficiency electrode is disposed in the sample receiving chamber, the sample sufficiency electrode is electrically connected to the power generator.

31. The biosensor of claim 26, wherein the electrically driven signal generator emits a visible, audible or tactile signal upon occurrence of the triggering event.

32. The biosensor of claim 31, wherein the test strip further defines a digital information zone in which is disposed a digital device.

33. The biosensor of claim 32, wherein the digital device comprises an electrical pattern encoded with information about the biosensor.

34. The biosensor of claim 26, wherein the test strip further defines a digital information zone in which is disposed a digital device.

35. The biosensor of claim 34, wherein the digital device comprises an electrical pattern encoded with information about the biosensor.

36. The biosensor of claim 26, wherein a reagent is disposed in the sample receiving chamber, the reagent at least partially covering an electrode set for estimating the concentration of an analyte contained in the fluid sample.

37. The biosensor of claim 36, further comprising a second electrode set at least partially disposed within the sample receiving chamber.

38. The biosensor of claim 36, wherein the sample receiving chamber includes a sample sufficiency electrode.

39. The biosensor of claim 26, wherein the test strip defines a substantially planar substrate on which is formed an electrical pattern extending into the measurement zone and power generation zone.

40. The biosensor of claim 39, further comprising at least one spacer or covering layer overlying the substantially planar substrate, the at least one spacer or covering layer having a void that defines the sample receiving chamber disposed in the measurement zone.

41. The biosensor of claim 40, wherein the sample receiving chamber includes a first electrode set which is covered by a reagent and which is electrically connected to the electrical pattern.

42. The biosensor of claim 41, further comprising a second electrode set disposed within the sample receiving chamber.

43. A biosensor for analyzing a fluid sample, comprising:
a test strip;
the test strip having a spacer layer, the spacer layer defining a first opening, a second opening, and a third opening;
the first opening defining a sample receiving chamber having a fluid receiving opening for receiving the fluid sample;
at least five electrical devices positioned on or in the test strip, each electrical device having a specific functionality, the electrical devices comprising first and second sets of electrodes, a power generator, a digital device, and an electrically driven signal generator;
wherein the first and second sets of electrodes are disposed at least partially within the sample receiving chamber, one of the first and second sets of electrodes determining the presence or estimating the concentration of an analyte in the fluid sample;
wherein the second opening is sized to receive the digital device, and the third opening is sized to receive the power generator; and
a user interface zone disposed on the test strip, the user interface zone having the electrically driven signal generator which emits a signal upon occurrence of a triggering event, the electrically driven signal generator includes a light disposed proximate the sample receiving chamber, the light illuminating the sample receiving chamber upon the occurrence of the triggering event.

44. The biosensor of claim 43, further comprising third and fourth sets of electrodes, wherein all four electrode sets are disposed at least partially within the sample receiving chamber.

45. The biosensor of claim 44, wherein each of the four electrode sets comprises the same functionality.

46. The biosensor of claim 44, wherein the sample receiving chamber has a volume of less than about 130 nl.

47. The biosensor of claim 44, wherein the four electrode sets comprises at least two different functionalities.

48. The biosensor of claim 44, wherein the four electrode sets comprises at least three different electrode functionalities.

49. The biosensor of claim 44, wherein the four electrode sets comprises four different electrode functionalities.

50. The biosensor of claim 44, wherein all four electrode sets are the same.

51. The biosensor of claim 44, wherein at least one of the electrode sets comprises a macro-electrode set and at least one other of the electrode sets comprises a micro-electrode set.

52. The biosensor of claim 43, wherein one of the electrical sets comprises a sample sufficiency electrode set in electrical communication with the sample receiving chamber.

53. The biosensor of claim 43, further comprising a third set of electrodes at least partially disposed within the sample receiving chamber for determining a correction factor for analyte concentration based on the detection of interferents in the fluid sample.

54. The biosensor of claim 43, wherein the electrically driven signal generator emits a visible, audible or tactile signal upon occurrence of the triggering event.

55. The biosensor of claim 43, wherein the signal generator comprises an OLED coated on an electrode set.

56. The biosensor of claim 55, wherein the electrode set comprises a micro-electrode array.

57. The biosensor of claim 56, wherein the micro-electrode set comprises substantially parallel, interdigitated fingers, each electrode of the micro-electrode set having at least two fingers.

58. The biosensor of claim 43, wherein the digital device comprises an electrode pattern encoded with digital information about the biosensor.

59. The biosensor of claim 58, wherein the digital information comprises lot code, expiration date or type of analyte.

60. The biosensor of claim 43, wherein the power generator comprises a battery.

61. The biosensor of claim 43, wherein the sample receiving chamber comprises first and second branches, the first electrode set being disposed in the first branch and the second electrode set being disposed in the second branch.

62. The biosensor of claim 61, wherein at least one of the first and second branches comprises at least two electrode sets.

63. A biosensor, comprising:
a test strip having a base substrate with an electrical pattern formed thereon, the test strip including a spacer layer and a transparent or translucent covering layer overlying the spacer layer, the spacer layer having a void that defines a sample receiving chamber disposed in a measurement zone which receives and analyzes a fluid sample;
a first electrode set formed on the base substrate and connected to the electrical pattern; and
an OLED coated on the first electrode set and operable to emit visible light upon application of a voltage across the first electrode set upon occurrence of a sufficient amount of said fluid sample being collected in said measurement zone, the spacer layer overlying the first electrode set, wherein the first electrode set is disposed proximate to and illuminates the measurement zone.

64. The biosensor of claim 63, wherein the OLED emits visible light when the voltage is less than about 10 volts.

65. The biosensor of claim 63, wherein the OLED emits visible light when the voltage is less than about 5 volts.

66. The biosensor of claim 63, wherein the OLED emits visible light when the voltage is less than about 3 volts.

67. The biosensor of claim 63, wherein the first electrode set comprises a micro-electrode set having substantially parallel interdigitated fingers.

68. The biosensor of claim 67, wherein each finger is spaced from the nearest adjacent finger by no more than about 25 μm.

69. The biosensor of claim 67, wherein each finger is spaced from the nearest adjacent finger by no more than about 5 μm.

70. The biosensor of claim 63, wherein the measurement zone comprises a sample receiving chamber in which is disposed a second set of electrodes for estimating the concentration of an analyte in the fluid sample.

71. The biosensor of claim 70, further comprising a third set of electrodes disposed in the sample receiving chamber.

72. A biosensor for analyzing a fluid sample, comprising:
a test strip;
the test strip defining a measurement zone having a sample receiving chamber in which is disposed a measurement electrode for detecting the presence or concentration of an analyte in the fluid sample, the sample receiving chamber including a reagent which reacts with the fluid sample, the test strip including a dosing edge wherein the sample receiving chamber is open at the dosing edge to receive the fluid sample;

the test strip further defining a user interface zone in which is disposed a numerical display which corresponds to concentration of an analyte in the fluid sample, wherein the user interface zone includes an electrically driven signal generator which emits a signal upon occurrence of a triggering event, the electrically driven signal generator includes a light disposed proximate the sample receiving chamber, the light illuminating the sample receiving chamber upon the occurrence of the triggering event; and the test strip including a meter insertion end having contacts thereon which are adapted to electrically connect to a meter.

73. The biosensor of claim 72, wherein the numerical display further comprises a plurality of micro-electrode arrays coated with an OLED.

74. The biosensor of claim 72, wherein the test strip is substantially flat.

75. The biosensor of claim 74, wherein the test strip comprises at least two substantially flat layers laminated together.

76. The biosensor of claim 75, wherein the at least two substantially flat layers cooperate to form the sample receiving chamber.

77. The biosensor of claim 76, wherein the sample receiving chamber is sized to draw in the fluid sample by capillary action.

78. The biosensor of claim 72, wherein the test strip is substantially flat and has a length of less than about 50 mm, a width is less than about 15 mm, and the thickness is less than about 1 mm.

79. The biosensor of claim 72, wherein the test strip has a thickness of less than about 5 mm.

* * * * *